United States Patent
Jones

(10) Patent No.: US 7,098,363 B1
(45) Date of Patent: Aug. 29, 2006

(54) PROCESS FOR THE PRODUCTION OF CARBOXYLIC ACID

(75) Inventor: Michael David Jones, Yorkshire (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/464,799

(22) Filed: Dec. 16, 1999

Related U.S. Application Data

(63) Continuation of application No. PCT/GB98/01726, filed on Jun. 12, 1998.

(30) Foreign Application Priority Data

Jun. 16, 1997 (GB) .............................. 9712601.5

(51) Int. Cl.
 *C07C 45/50* (2006.01)
(52) U.S. Cl. ........................................ 562/519; 560/97
(58) Field of Classification Search ................ 562/519; 560/97
 See application file for complete search history.

(56) References Cited

U.S. PATENT DOCUMENTS

| 4,328,125 A | 5/1982 | Drago et al. |
| 4,625,049 A | 11/1986 | Current |
| 4,628,113 A | 12/1986 | Current |
| 4,874,558 A | 10/1989 | Fife et al. |
| 5,155,261 A | 10/1992 | Marston et al. |
| 5,334,755 A | 8/1994 | Yoneda et al. |
| 5,360,929 A | 11/1994 | Watson et al. |
| 5,364,963 A | 11/1994 | Minami et al. |

FOREIGN PATENT DOCUMENTS

| EP | 0 250 189 A1 | 12/1987 |
| EP | 0 260 189 A1 | 12/1987 |
| EP | 0 759 416 A1 | 2/1997 |
| WO | 94/05423 | 3/1994 |

OTHER PUBLICATIONS

Derwent Abstract 97-435993, "Imidazole(s)-rhodium catalyst and its preparation," XP-002077608.

Dazhi et al, Appl. No. 95104298.x, "Imidazole-type Polymeric Rhodium . . . ," (1996).

Yuan et al, "Preparation and Catalytic Activities of . . . ," Organomet- Compd-Synth., Struct. Theory, pp. 244-259.

Halttunen et al, "Liquid phase methanol hydrocarbonylation with homogeneous . . . ," Journ. of Mol. Catalysis A: Chemical, 109 pp. 209-217 (1996).

Tempesti et al, "$C_2$+ Carboxylic acids by catalytic carbonylation . . . " Chemistry & Industry, pp. 548-549 (1991).

WPIDS Abstract 1994-362746, "Reactor for catalytic reaction using circulating . . . ".

WPIDS Abstract 1996-045336, "Mfg. organic carboxylic acids with small iodide content . . . ".

WPIDS Abstract 1994-316511, "Acetic anhydride preparation using solid catalyst . . . ".

WPIDS Abstract 1998-315295, "Production of acetic acid—where concentration of rhodium complex . . . ".

Yuan et al, "A Novel Copolymer—Bound Cis-Dicarbonylrhodium Complex . . . ," Chinese Journal of Polymer Science, vol. 7, No. 3, pp. 219-224 (1989).

Yuan et al, "Kinetic Study of Carbonylation of Methanol to Acetic Acid and Acetic . . . ," Chinese Journal of Polymer Science, vol. 7, No. 3, pp. 225-231 (1989).

ACS Abstract CA113(9):77425b, "Synthesis, structure and catalytic activity of a series . . . ".

ACS Abstract CA110(22): 195043m, "Structure and catalytic activity of *rhodium* complex . . . ".

*Primary Examiner*—Shaojia Jiang
*Assistant Examiner*—Ganapathy Krishnan
(74) *Attorney, Agent, or Firm*—Nixon & Vanderhye

(57) ABSTRACT

A process for the production of a product comprising a carboxylic acid having n+1 carbon atoms which process comprises reacting in the liquid phase at elevated temperature and pressure a composition comprising an alcohol having n carbon atoms and/or a reactive derivative thereof, a halogen and/or a halogen compound promoter, water and carbon monoxide in the presence of hydrogen and a heterogeneous catalyst comprising a Group VIII noble metal species on a polymeric resin having a functional group selected from nitrogen-containing heterocycles.

23 Claims, No Drawings

PROCESS FOR THE PRODUCTION OF CARBOXYLIC ACID

This is a continuation of PCT application PCT/GB98/01726, filed 12 Jun. 1998, the entire content of which is hereby incorporated by reference in this application.

The present invention relates in general to the production of a carboxylic acid by the carbonylation of an alcohol and/or a reactive derivative thereof and in particular to the production of a carboxylic acid by the carbonylation of an alcohol and/or a reactive derivative thereof in the liquid phase in the presence of water and a heterogeneous carbonylation catalyst.

The production of acetic acid by the rhodium-catalysed, iodide-promoted carbonylation of methanol in a homogeneous liquid-phase reaction medium is a well-known process and is operated on a commercial scale. It has been recognised for some time that the presence of water in the carbonylation reaction is desirable because it accelerates the carbonylation reaction and improves the selectivity to the desired product. The desirability of employing heterogeneous carbonylation catalysts for the purpose of facilitating product separation from the catalyst has also been recognised. Heterogeneous carbonylation catalysts and their use are described in a number of patent publications including, for example U.S. Pat. No. 5,155,261; EP-A-656811; U.S. Pat. No. 5,364,963; and U.S. Pat. No. 5,360,929.

U.S. Pat. No. 5,155,261 discloses a process for preparing acetic acid, comprising the step of reacting methanol with carbon monoxide under pressures of about 65–80 Bar and a temperature of about 170–200° C. in the presence of an iodide promoter acid and a catalyst comprising an insoluble polymer having pendant free base, N-oxide or quaternised pyridine groups supporting a rhodium species loaded to less than about 10 weight percent (expressed as metal) of the polymer component.

EP-A-656811 discloses a catalyst composition for use in carbonylation comprising a polymer having pendant pyrrolidone groups supporting a rhodium species, and a catalyst promoter comprising an alkyl iodide.

U.S. Pat. No. 5,364,963 discloses a catalyst for the production of acetic acid from methanol and carbon monoxide comprising a rhodium complex supported on a porous, cross-linked vinyl pyridine resin, wherein said vinyl pyridine resin has a cross-linking degree of 30–60%, a pore volume of 0.2–0.4 cc/g and an average-pore diameter of 20–100 nm.

Finally, U.S. Pat. No. 5,360,929 discloses a process for the production of a carboxylic acid anhydride which process comprises contacting a reaction composition comprising a carboxylic acid ester, a hydrocarbyl halide and/or a hydrocarbyl ether reactant and a hydrocarbyl halide promoter with carbon monoxide in the presence of a catalyst comprising an insoluble polymer support having pendant quaternised N-base or alkylated N-oxide pyridine groups supporting a rhodium species in which process there is maintained throughout the process a finite concentration of carboxylic acid anhydride in the reaction composition.

A problem associated with the use of heterogeneous catalysts in carbonylation processes is that of leaching of the catalytic species, typically rhodium, from the support material. Thus, in U.S. Pat. No. 5,360,929 it is stated:—

"It has now been found, contrary to the description of U.S. Pat. No. 5,155,261, that rhodium is leached from a polymer support under typical carbonylation conditions of high pressure and temperature in the presence of an aqueous liquid phase. Such leaching of rhodium may present difficulties, for example requiring recovery of the rhodium if the process is to be operated continuously".

The problem is also mentioned in, for example, EP-A-0567331, which states as follows:—

"Continuous carbonylation of methanol in the presence of methyl iodide promoter using a flow type reactor having a fixed bed of a rhodium supporting polymer catalyst is shown in Hortkjaer et al, Applied Catalysis, 67, 269–278 (1991). According to this report, however, the leaching out of rhodium considerably occurs so that, about several hours after the commencement of the reaction, the intrinsic activity is about 4.6 times lower than for the homogeneous catalyst".

The problem to be solved then is that of reducing leaching of the active catalytic species from the support material during the carbonylation of an alcohol and/or a reactive derivative thereof in the liquid phase in the presence of water and a heterogeneous carbonylation catalyst to produce a product comprising a carboxylic acid. We have found that a solution to the problem is to conduct the carbonylation in the additional presence of hydrogen.

Hydrogen has been used before in carbonylation reactions. Thus, the aforesaid U.S. Pat. No. 5,360,929 mentions that hydrogen may be present as a co-promoter in the carbon monoxide feedstock, the solution to the problem of rhodium leaching from the heterogeneous catalyst being the maintenance throughout the process of a finite concentration of carboxylic acid anhydride in the reaction composition. The patent emphasises that by using a reaction composition in which there is maintained a finite concentration of carboxylic acid anhydride the reaction composition is maintained substantially anhydrous and substantially no water and/or alcohol will be present in the reaction composition. This differs from the process of the present invention in which both water and alcohol or reactive derivative thereof are present in the reaction composition and the product comprises acetic acid.

In EP-B-0250189 there is also described a carbonylation process in the presence of hydrogen. In this process a lower carboxylic acid is produced by reacting a feed consisting essentially of an alcohol having one less carbon atom than said acid with carbon monoxide in a carbonylation reactor holding a liquid reaction medium containing a rhodium catalyst, the process comprising maintaining in said reaction medium during the course of said reaction a quantity of water together with (a) a catalyst stabiliser selected from iodide salts which are soluble in said reaction medium at reaction temperature, (b) the iodide derivative of a lower hydrocarbon corresponding to said alcohol and (c) the ester of said alcohol with said carboxylic acid, characterised in that there is also maintained a partial pressure of hydrogen of at least 4 psi (27.58 kPA) at reaction conditions and the quantity of water is less than 14% by weight of said reaction medium. The invention does not address the problem of active catalytic species leaching from the support during heterogeneously catalysed carbonylation, indeed throughout the disclosure there is no mention of the use of a heterogeneous carbonylation catalyst.

Accordingly the present invention provides a process for the production of a product comprising a carboxylic acid having n+1 carbon atoms which process comprises reacting in the liquid phase at elevated temperature and pressure a composition comprising an alcohol having n carbon atoms and/or a reactive derivative thereof, a halogen and/or a halogen compound promoter, water and carbon monoxide in the presence of hydrogen and a heterogeneous catalyst comprising a Group VIII noble metal species on a polymeric resin having functional groups selected from nitrogen-containing heterocycles.

The alcohol having n carbon atoms may suitably be an aliphatic alcohol having 1 to 12 carbon atoms, preferably 1 to 6 carbon atoms, including methanol, ethanol, propanol and isopropanol, butanols, pentanols and hexanols. A preferred alcohol is methanol, the carbonylation product of which comprises acetic acid and/or methyl acetate. Reactive derivatives of the alcohol which may be used as an alternative, or additional thereto, include dialkyl ethers having n carbon atoms and esters of alcohols having n carbon atoms with carboxylic acids having n+1 carbon atoms. Suitable reactive derivatives of methanol, for example, include methyl acetate, dimethyl ether and methyl iodide. A mixture of more than one alcohol and/or reactive derivative thereof, for example a mixture of methanol and methyl acetate, may also be employed.

As promoter there may be used either a halogen or a halogen compound, which may be for example a hydrogen halide, an alkyl or an aryl halide, a metal halide or an ammonium, phosphonium, arsonium or stibonium halide. Promoters containing iodide as the halogen moiety are preferred. Preferably the promoter is an alkyl iodide, preferably an alkyl iodide having an alkyl moiety corresponding to the alcohol and/or its reactive derivative reactant, for example methyl iodide.

Water is an essential component of the reaction mixture in the process of the present invention. Suitably water may be present in an amount greater than 0.1% up to 25% by weight based on the weight of the reaction mixture. Typically two ranges may be distinguished within the aforesaid broad range, a first being from greater than 0.1 to 6.0%, preferably from about 0.5 to 4% by weight, which may be termed 'low water' conditions and the second being from greater than 6.0 to 25%, preferably from 8 to 18% by weight, which may be termed 'high water' conditions. Water is in general produced during the carbonylation process as a by-product of esterification. This water may be recycled to the reaction mixture. Generally it will be necessary, especially for 'high water' conditions, to include water in the reaction composition.

The carbon monoxide reactant may be essentially pure or may contain impurities such as carbon monoxide, methane, nitrogen, noble gases and $C_1$ to $C_4$ paraffinic hydrocarbons.

The hydrogen essential to the performance of the present invention may be fed with the carbon monoxide reactant or may be fed separately therefrom. In a continuous process the hydrogen may be fed either continuously or intermittently. The amount of hydrogen required to achieve the benefits of the present invention will vary depending upon at least the particular reaction conditions employed. Typically, the hydrogen partial pressure may be from 0.1 to 10 bar, preferably 0.4 to 8 bar, especially 1 to 4 bar.

The heterogeneous catalyst employed comprises a Group VIII noble metal on a support. The noble metal is bound to a polymeric resin having a functional group selected from nitrogen-containing heterocycles. The polymeric resin may be an unsubstituted imidazole or substituted imidazole such as 2-pyridyl-2-imidazole, benzimidazole, 5-benzimidazole carboxylic acid and hydroxy substituted imidazoles and benzimidazoles.

The polymer may also be a polymer having pendant quaternised N-base or alkylated N-oxide pyridine groups. Preferably the polymer resin is a porous cross-linked 4- or 2-vinyl pyridine copolymer in the free base or N-oxide form which has been respectively quaternised or alkylated in situ with a hydrocarbyl halide. Suitable hydrocarbyl halides are those described hereinbefore in relation to halogen compound promoters.

More preferably the polymer resin is prepared from a porous cross-linked poly (4- or 2-vinyl pyridine) copolymer such as those commercially available from Reilly Industries Inc. under the REILLEX™ family of trademarks. Examples of these are Reillex™ 225, Reillex™ 402, Reillex™ 425 and Reillex HP resin. In these Reillex TM copolymers pyridine rings are attached directly at their 4- or 2-positions to the polymer backbone which is in turn cross-linked with some percentage of divinyl benzene being present. Reillex™ 425, for example, is a preferred polymer, being a 25% cross-linked copolymer of 4-vinyl pyridine and a commercially available divinyl benzene exhibiting a convenient insoluble bead form, high porosity, good thermal stability, and high concentration of metal binding sites. Reillex™ 425 is typically available in bead sizes of approximately 18-50 mesh. The temperature stability for extended use of Reillex™ 425 polymer is about 260° C., which is particularly practical for commercial carbonylation processes.

Other preferred polymers include, for example, other cross-linked poly (4- and 2-vinyl pyridine) copolymers such as those commercially available under the Reillex™ 402 and 225 trademarks. Of these, Reillex™ 225 is a 25% cross-linked copolymer of 2-vinyl pyridine and a commercially available divinyl benzene. Reillex™ 402 is a 2% cross-linked copolymer of 4-vinyl pyridine and a commercially available divinyl benzene. In other relevant aspects Reillex™ 225 is similar in its performance to the Reillex™ 425 described hereinbefore. Reillex™ 402 is a granular powder, in contrast to the bead forms of Reillex™ 225 and 425, with a particle size of about 60 mesh and a slightly lower, but still acceptable, maximum temperature for extended use of about 225° C.

In addition to the Reillex™ polymers, other polymers having pyridine, or pyridyl groups are suitable for preparing the catalyst of the present invention. These include polymers such as KEX™ 316 polymeric amine resin. Cross-linked polymers containing vinyl pyridines may be prepared by reaction of the appropriate vinyl pyridine, divinyl benzene and styrene in toluene and in the presence of benzoyl peroxide and an aqueous solution of hydrocellulose, sodium chloride and sodium hydride. Further details of the poly (4- and 2-vinyl pyridine) copolymers and their preparation may be found in U.S. Pat. No. 5,155,261.

The Group VIII noble metal species is any Group VIII noble metal-containing compound which is capable of binding to the pendant quaternised or alkylated pyridine groups of the insoluble polymer support to give an active carbonylation catalyst. Suitably the metal is rhodium or iridium.

Examples of suitable rhodium-containing compounds useful in the preparation of the heterogeneous catalyst are $RhCl_3$, $[\{Rh(CO)_2Cl_2\}]$, $RhC_1$ hydrate, $RhBr_3$ hydrate, $RhI_3$, $Rh(OH)_3$, $Rh_2O_3$ and rhodium acetate.

Examples of suitable iridium-containing compounds useful in the preparation of the heterogeneous catalyst include $IrCl_3$, $[IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^{-H+}$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates.

The metal species on the support is present typically at up to 8% by weight of supported catalyst, preferably 0.05 to 4% by weight.

The heterogeneous catalyst preferably further comprises a promoter. Suitable promoters are selected from ruthenium, osmium, tungsten, rhenium, zinc, cadmium, indium, gallium and mercury. Preferably, the promoter is selected from ruthenium and osmium.

Examples of suitable ruthenium-containing compounds useful in the preparation of the promoted heterogeneous catalyst include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, tetra(aceto)chlororuthenium (II,III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium (II), tetrachlorobis(benzene)diruthenium(II), dichloro(cycloocta-1,5-diene)ruthenium (II) polymer and tris(acetylacetonate) ruthenium (III).

Examples of suitable osmium-containing compounds useful in the preparation of the promoted heterogeneous catalyst include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$pentachloro-µ-nitrododiosmium and mixed osmium halocarbonyls such as tricarbonyldichloroosmium (II) dimer and other organoosmium complexes.

Examples of suitable tungsten-containing compounds which may be used as sources of promoter include $W(CO)_6$, $WCl_4$, $WCl_6$, $WBr_5$, $WI_2$, or $C_9H_{12}$ $W(CO)_3$ and any tungsten chloro-, bromo- or iodo-carbonyl compound.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $Re(CO)_4I_2]^-H+$ and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$ and zinc acetylacetonate.

Examples of suitable gallium-containing compounds which may be used as sources of promoter include gallium acetylacetonate, gallium acetate, $GaCl_3$, $GaBr_3$, $GaI_3$, $Ga_2Cl_2$ and $Ga(OH)_3$.

Examples of suitable indium-containing compounds which may be used as sources of promoter include indium acetylacetonate, indium acetate, $InCl_3$, $InBr_3$, $InI_3$, $InI$ and $In(OH)_3$.

The molar ratio of each promoter to the Group VIII metal species is suitably in the range 0.1:1 to 15:1, preferably 0.5:1 to 10:1.

The process of the invention is suitably operated at a total pressure in the range from 1 to 500 barG, preferably from 10 to 60 barG.

The process is suitably performed at a temperature in the range from 50 to 250° C., the practical upper operating temperature being dependant on the thermal stability of the catalyst. Preferably the temperature is in the range 100 to 200° C., most preferably in the range 150 to 200° C.

The process may be operated as a batch or continuous process, preferably as a continuous process.

The invention will now be illustrated by reference to the following comparison tests and examples.

Preparation of Pre-Formed Catalyst from REILLEX™ 425 Resin

The resin was supplied (by Reilly Industries Inc.) wet to the touch (40–50%). The water was removed with methanol. The dried resin was quaternised with excess methyl iodide at room temperature and pressure in methanol solvent. The resin was then washed with methanol to remove unreacted methyl iodide and air-dried.

Experimental

All experiments were performed using 300 ml Hastelloy B2 (Trade Mark) autoclave equipped with a Dispersimax (Trade Mark) stirrer, liquid catalyst injection facility, in-situ liquid sampling system, and cooling coils. A gas supply to the autoclave was provided from a ballast vessel, feed gas being provided to maintain the autoclave at a constant pressure. The rate of gas uptake at a certain point in a reaction run was used to calculate the rate, rhodium turnovers (moles acetic acid/mole rhodium/h), at a particular reactor composition (reactor composition based on a cold degassed volume).

For each batch carbonylation experiment the Reillex resin was charged to the autoclave. The reactor was then pressure tested with nitrogen and vented via a gas sampling system. The autoclave was then flushed with carbon monoxide (3×5 barG). The remaining liquid components of the reaction composition were then charged to the autoclave via a liquid addition port. The autoclave was then pressurised with carbon monoxide (typically 4 barG) and heated with stirring (1500 rpm) to reaction temperature, 190° C. The total pressure was then raised to the desired operating pressure, 30 barG by feeding forward carbon monoxide from the ballast vessel. The reactor pressure was maintained (±0.5 barG) by feeding gas from the ballast vessel throughout the experiment. Gas uptake from the ballast vessel was measured using datalogging facilities throughout the course of the experiment. The actual reaction temperature was maintained within ±1° C. of the desired reaction temperature by means of a heating mantle connected to a Eurotherm (Trade Mark) controller. In addition, excess heat of reaction was removed by means of cooling coils. At the end of the reaction the ballast vessel was isolated and a sample system was flushed with reactor liquid and then a sample was taken and was analysed for rhodium by ICP. The reactor was then crash cooled by use of the cooling coils. The head space gases and liquid product were sampled and analysed by gas Chromatography.

Comparison Test 1

Baseline Reaction Under 'Low Water' Conditions

The batch autoclave was charged with Reillex 425 resin (25 ml 15.8 g) prior to pressure testing. The autoclave was charged with methyl iodide (20 g, 0.14 moles), acetic acid (54.9 g, 0.91 moles), methyl acetate (50.1 g, 0.68 moles), water (13 g, 0.72 moles) and $[Rh(CO)_2Cl]_2$ (0.128 g, 0.33 mmoles) dissolved in acetic acid (12.0 g, 0.2 moles)

When the methyl acetate concentration (carbon monoxide) was calculated to be 20% by weight the reaction rate was calculated to be 1098 Rh turnovers/hr. At 10% by weight methyl acetate concentration the reaction rate was 586 Rh turnovers/hr.

The liquid sample contained 0.7 ppm Rh at 7.5% methyl acetate, 2.3% water and 12.2% methyl iodide.

Comparison Test 2

Baseline Reaction Under 'High Water' Conditions

The batch autoclave was charged with Reillex 425 resin (25 ml 15.8 g) prior to pressure testing. The autoclave was charged with methyl iodide (20 g, 0.14 moles), acetic acid (48.0 g, 0.80 moles), methyl acetate (50.0 g, 0.68 moles), water (20 g, 1.11 moles) and $[Rh(CO)_2Cl]_2$ (0.12 g, 0.33 mmoles) dissolved in acetic acid (12.0 g, 0.2 moles).

When the methyl acetate concentration (carbon monoxide) was calculated to be 20% by weight the reaction rate was calculated to be 1558 Rh turnovers/hr. At 10% by weight methyl acetate concentration the reaction rate was 892 Rh turnovers/hr.

The liquid sample contained 20.8 ppm Rh at 5.5% methyl acetate, 6.1% water and 12.1% methyl iodide.

Comparison Test 1 and 2 are not examples according to the present invention because the carbonylations were conducted in the absence of hydrogen. They are included only for the purpose of comparison.

EXAMPLE I

Carbonylation in the Presence of Hydrogen Under 'Low Water' Conditions

The batch autoclave was charged with Reillex 425 resin (25 ml 15.3 g) prior to pressure testing. The autoclave was flushed with Hydrogen (3×5 barG) then the autoclave was charged with methyl iodide (20.1 g, 0.14 moles), acetic acid 55.6 g, 0.93 moles), methyl acetate (50.0 g, 0.68 moles), water (13.0 g, 0.72 moles) and $[Rh(CO)_2Cl]_2$ (0.1298 g, 0.33 mmoles) dissolved in acetic acid (12.0 g 0.2 moles). The autoclave was pressurised with 1 barG hydrogen and then 3 bar carbon monoxide prior to heating.

When the methyl acetate concentration was calculated to be 20% by weight the reaction rate was calculated to be 1166 Rh turnovers/hr. At 10% by weight methyl acetate concentration the reaction rate was 606 Rh turnovers/hr.

The liquid sample contained 0.2 ppm Rh at 6.4% methyl acetate, 2.1% water and 12.1% methyl iodide.

EXAMPLE 2

Carbonylation in the Presence of Hydrogen Under 'High Water' Conditions

The batch autoclave was charged with Reillex 425 resin (25 ml 13.2 g) prior to pressure testing. The autoclave was flushed with Hydrogen (3×5 barG) then the autoclave was charged with methyl iodide (20.0 g, 0.14 moles), acetic acid (47.9 g, 0.80 moles), methyl acetate (50.0 g, 0.68 moles), water (20.0 g, 1.11 moles and $[Rh(CO)_2Cl]_2$ (0.127 g, 0.33 mmoles) dissolved in acetic acid (12.0 g 0.2 moles). The autoclave was pressurised with 1 barG hydrogen and then 3 bar carbon monoxide prior to heating.

When the methyl acetate concentration was calculated to be 20% by weight the reaction rate was calculated to be 1584 Rh turnovers/hr. At 10% by weight methyl acetate concentration the reaction rate was 926 Rh turnovers/hr.

The liquid sample contained 12.1 ppm Rh at 7.1% methyl acetate, 6.5% water and 12.2% methyl iodide.

EXAMPLE 3

Carbonylation in the Presence of Hydrogen Under 'High Water' Conditions

The batch autoclave was charged with Reillex 425 resin (25 ml 13.4 g) prior to pressure testing. The autoclave was flushed with Hydrogen (3×5 barG) then the autoclave was charged with methyl iodide (20.1 g, 0.14 moles), acetic acid (48.5 g, 0.81 moles), methyl acetate (50.0 g, 0.68 moles), water (20.0 g, 1.11 moles) and $[Rh(CO)_2Cl]_2$ (0.126 g, 0.32 mmoles) dissolved in acetic acid (12.0 g, 0.2 moles). The autoclave was pressurised with 4 barG hydrogen and then 9 bar carbon monoxide prior to heating. The total pressure of the autoclave during the reaction was maintained at 33 barG, (i.e. maintain partial pressure of carbon monoxide for comparison with Comparison Test 2).

When the methyl acetate concentration was calculated to be 20% by weight the reaction rate was calculated to be 1913 Rh turnovers/hr. At 10% by weight methyl acetate concentration the reaction rate was 1113 Rh turnovers/hr.

The liquid sample contained 15.2 ppm Rh at 4.6% methyl acetate, 5.8% water and 12.1% methyl iodide.

We claim:

1. A process for the production of a product comprising a carboxylic acid having n+1 carbon atoms which process comprises reacting in the liquid phase at elevated temperature and pressure a composition comprising an alcohol having n carbon atoms and/or a reactive derivative thereof, a halogen and/or a halogen compound promoter, water and carbon monoxide in the presence of hydrogen and a heterogeneous catalyst comprising a Group VIII noble metal species on a polymeric resin having a functional group selected from nitrogen-containing heterocycles.

2. A process as claimed in claim 1 wherein the alcohol is an aliphatic alcohol having 1 to 12 carbon atoms.

3. A process as claimed in claim 1 wherein the promoter is selected from hydrogen halide, an alkyl halide, aryl halide, a metal halide, ammonium halide, phosphonium halide, arsonium halide and stibonium halide.

4. A process as claimed in claim 1 wherein water is present at a concentration of 0.1 to 25% by weight based on the weight of reaction mixture.

5. A process as claimed in claim 4 wherein water is present at a concentration of 0.1 to 6.0% by weight based on the weight of the reaction mixture.

6. A process as claimed in claim 5 wherein water is present at a concentration of 0.5 to 4% by weight based on the weight of the reaction mixture.

7. A process as claimed in claim 1 wherein the hydrogen is present at a partial pressure of from 0.1 to 10 bar.

8. A process as claimed in claim 4 wherein the hydrogen is present at a partial pressure of from 0.1 to 10 bar.

9. A process as claimed in claim 5 wherein the hydrogen is present at a partial pressure of from 0.1 to 10 bar.

10. A process as claimed in claim 6 wherein the hydrogen is present at a partial pressure of from 0.1 to 10 bar.

11. A process as claimed in claim 1 wherein the Group VIII noble metal is rhodium or iridium.

12. A process as claimed in claim 8 wherein the Group VIII noble metal is rhodium or iridium.

13. A process as claimed in claim 9 wherein the Group VIII noble metal is rhodium or iridium.

14. A process as claimed in claim 10 wherein the Group VIII noble metal is rhodium or iridium.

15. A process as claimed in claim 1 in which the polymer resin is an unsubstituted or substituted imidazole.

16. A process as claimed in claim 15 wherein the polymer resin is polybenzimidazole.

17. A process as claimed in claims 1 wherein the polymer resin is a porous cross linked 4 or 2-vinyl pyridine copolymer in the free base or N-oxide form.

18. A process as claimed in claims 7 wherein the polymer resin is a porous cross linked 4 or 2-vinyl pyridine copolymer in the free base or N-oxide form.

19. A process as claimed in claims 8 wherein the polymer resin is a porous cross linked 4 or 2-vinyl pyridine copolymer in the free base or N-oxide form.

20. A process as claimed in claims 9 wherein the polymer resin is a porous cross linked 4 or 2-vinyl pyridine copolymer in the free base or N-oxide form.

21. A process as claimed in claims 10 wherein the polymer resin is a porous cross linked 4 or 2-vinyl pyridine copolymer in the free base or N-oxide form.

22. A process as claimed in claim 12 wherein the polymer resin is a porous cross linked 4 or 2-vinyl pyridine copolymer in the free base or N-oxide form.

23. A process as claimed in claim 12 carried out at a temperature of 50 to 250° C. and a pressure of 1 to 500 barg G.

* * * * *